United States Patent [19]

Mori et al.

[11] Patent Number: 4,942,262

[45] Date of Patent: Jul. 17, 1990

[54] PROCESS FOR PRODUCING VITAMIN A OR ITS CARBOXYLIC ACID ESTERS

[75] Inventors: Toshiki Mori; Shigeaki Suzuki; Takashi Onishi, all of Kurashiki, Japan

[73] Assignee: Kuraray Company Ltd., Kurashiki, Japan

[21] Appl. No.: 368,800

[22] Filed: Jun. 20, 1989

[30] Foreign Application Priority Data

Jul. 5, 1988 [JP] Japan .................................. 63-168190
Jul. 5, 1988 [JP] Japan .................................. 63-168191

[51] Int. Cl.$^5$ .......................................... C07C 147/00
[52] U.S. Cl. .......................................... 568/32; 568/28
[58] Field of Search ...................................... 568/32, 28

[56] References Cited

U.S. PATENT DOCUMENTS 4,825,006  4/1989  Otera et al. ............................ 568/32

OTHER PUBLICATIONS

Otera et al. Chemical Abstracts, vol. 106, p. 5258, 1987.

*Primary Examiner*—Anton H. Sutto
*Assistant Examiner*—Deborah D. Carr
*Attorney, Agent, or Firm*—Oblon, Spivak, McClelland, Maier & Neustadt

[57] ABSTRACT

The invention provides a process for producing vitamin A or its carboxylic acid ester by treating inexpensive and readily available industrial starting materials with potassium hydroxide which is widely employed industrially and is inexpensive.

12 Claims, No Drawings

PROCESS FOR PRODUCING VITAMIN A OR ITS CARBOXYLIC ACID ESTERS

BACKGROUND OF THE INVENTION

1. Field of the Invention

This invention relates to a process for producing vitamin A or its carboxylic acid esters. Vitamin A or its carboxylic acid esters, typical of which are the acetate and palmitate, are used in large quantities as medicines, feed additives and the like.

2. Description of the Prior Art

For the production of vitamin A, there is known, as described in European Patent Publication No. 0 187 259, a process wherein halogenated sulfones are treated with bases in hydrocarbon solvent according to the following reaction sequence to obtain vitamin A.

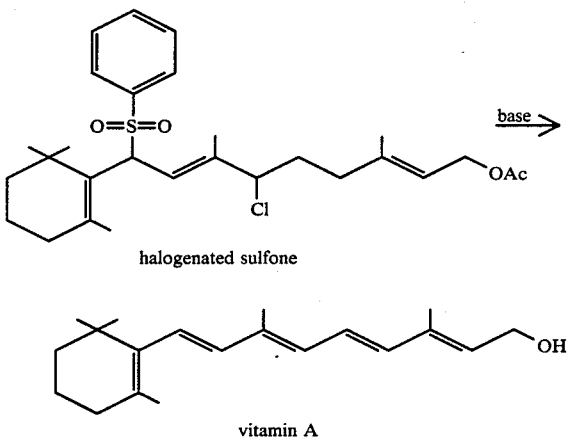

halogenated sulfone

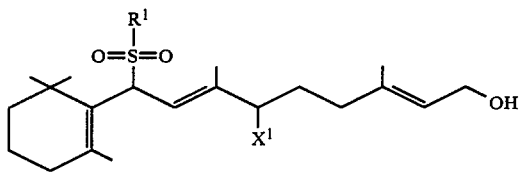

vitamin A

According to the above known process, when a halogenated sulfone used as a starting material for the reaction is treated with a potassium alkoxide, vitamin A can be obtained in relatively high yield. However, the potassium alkoxide has the problem with respect to availability and cost, thus leaving much room for improvement.

SUMMARY OF THE INVENTION

An object of the invention is to provide a process for efficiently producing vitamin A or its carboxylic acid esters using bases which are widely used industrially and are inexpensive.

According to the invention, the above object can be achieved by a process which comprises (i) treating a halogenated sulfone of the general formula (1)

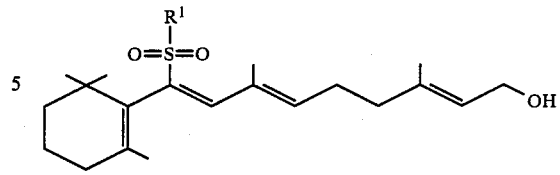

wherein $R^1$ represents a phenyl group which may be substituted and $X^1$ represents a halogen atom, and/or a vinyl sulfone of the general formula (2)

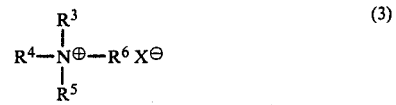

wherein $R^1$ has the same meaning as defined above, with potassium hydroxide in a hydrocarbon solvent in the presence of a quaternary ammonium salt of the general formula (3) or a crown ether $$R^4-\overset{\overset{R^3}{|}}{\underset{\underset{R^5}{|}}{N^\oplus}}-R^6\ X^\ominus \quad (3)$$

wherein $R^3$, $R^4$, $R^5$ and $R^6$ are the same or different and represents an alkyl group or an aralkyl group, and X represents a halogen atom, a lower alkoxy group, an acyloxy group, a hydrogensulfate or a hydroxyl group, or (ii) treating a halogenated sulfone of the general formula (4)

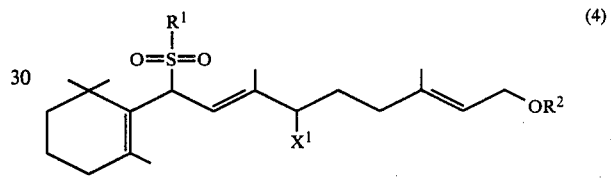

wherein $R^1$ and $X^1$ have, respectively, the same meanings as defined above, and $R^2$ represents a lower acyl group, with potassium hydroxide in a hydrocarbon or ether solvent in the presence of a quaternary ammonium salt of the above-indicated general formula (3) and an alcohol of the general formula (5)

wherein $R^7$, $R^8$ and $R^9$ are the same or different and represent a hydrogen atom, an alkyl group which may be substituted with an oxygen atom, an aryl group or an aralkyl group. The resultant vitamin A may be acylated, if necessary.

Vitamin A and its carboxylic acid esters include as isomers a 9-cis isomer, a 11-cis isomer, a 13-cis isomer, a 11,13-dicis isomer, a 9,13-dicis isomer, and an all-trans isomer. Of these, the all-trans isomer is considered to exhibit the highest biological activity. One of features according to the invention resides in the production, in high yield, of vitamin A or its carboxylic acid esters which have a high content of the all-trans isomer.

DESCRIPTION OF THE PREFERRED EMBODIMENTS $R^1$, $R^2$, $X^1$, $R^3$, $R^4$, $R^5$, $R^6$ and X in the above general formulae are described in detail.

$R^1$ represents a phenyl group which may be substituted. Examples of the substituent include: lower alkyl groups such as a methyl group, an ethyl group, an i-propyl group, an n-propyl group, an i-butyl group, an n-butyl group and the like; halogen atoms such as a chlorine atom, a bromine atom, an iodine atom and the like; and lower alkoxy groups such as a methoxy group, an ethoxy group, an i-propoxy group, an n-propoxy group, an i-butoxy group, an n-butoxy group and the like. The substituent may be at any of ortho, meta and para positions and one or more substituents may be joined. $R^2$ represents a lower acyl group such as a formyl group, an acetyl group, a propionyl group or the like. $X^1$ represents a halogen atom such as a chlorine atom, a bromine atom, an iodine atom or the like.

$R^3$, $R^4$, $R^5$ and $R^6$ independently represent an alkyl group or an aralkyl group. The alkyl group is preferably one which is linear or branched and has from 1 to 20 carbon atoms. Specific examples include a methyl group, an ethyl group, an n-propyl group, an i-propyl group, an n-butyl group, a pentyl group, a hexyl group, a heptyl group, an octyl group, a nonyl group, a decyl group, a dodecyl group, a tridecyl group, an octadecyl group, a nonadecyl group and the like. Examples of the aralkyl group include a benzyl group, a 1-phenylethyl group, a 2-phenylethyl group, a 3-phenylpropyl group and the like. X represents a halogen atom, a lower alkoxy group, an acyloxy group, a hydrogensulfate ($HSO_4$—) group or a hydroxyl group. The halogen atom includes a chlorine atom, a bromine atom, an iodine atom or the like. Examples of the lower alkoxy group include a methoxy group, an ethoxy group, a propoxy group, an n-butoxy group, a t-butoxy group and the like. Examples of the acyloxy group include a lower alkylcarbonyloxy group such as a formyloxy group, an acetoxy group, a propionyloxy group or the like, and an arylcarbonyloxy group such as a benzoyloxy group.

Specific examples of the quaternary ammonium salts of the general formula (3) include tetraethylammonium chloride, tetraethylammonium bromide, tetraethylammonium iodide, tetra-n-butylammonium chloride, tetra-n-butylammonium bromide, tetra-n-butylammonium hydrogensulfate, tetra-n-butylammonium methoxide, benzyltrimethylammonium chloride, stearyltrimethylammonium chloride and the like. The amount of the quaternary ammonium chloride is in the range of from 0.1 to 100 mole %, preferably from 1 to 5 mole %, based on the halogenated sulfone of the general formula (1) and/or the vinyl sulfone of the general formula (2) for the reaction of (i) and is in the range of from 0.1 to 100 mole %, preferably from 1 to 5 mole %, based on the halogenated sulfone of the general formula (4) for the reaction of (ii).

The reaction (i) according to the invention is described.

The crown ether used in the reaction is a cyclic polyether which has at least four atoms capable of coordination relative to metal ions, e.g. an oxygen atom, a nitrogen atom and a sulfur atom, at portions joined to form the ring. Examples of the crown ether include 12-crown-4, 15-crown-5, 18-crown-6, dibenzo-18-crown-6, dicyclohexyl-18-crown-6 and the like. The amount of the crown ether is generally in the range of from 0.1 to 100 mole %, preferbly from 1 to 10 mole %, based on the halogenated sulfone of the general formula (1) and/or the vinyl sulfone of the general formula (2). This reaction should be effected, preferably in an atmosphere of an inert gas, in a hydrocarbon solvent. Examples of the hydrocarbon solvent include toluene, benzene, hexane, cyclohexane and the like. The amount of the solvent is preferably determined such that the concentration of the starting materials, i.e. the halogenated sulfone and/or the vinyl sulfone, is in the range of about 0.05 to 2 moles/liter.

The reaction is carried out at a temperature ranging from $-10°$ C. to 100° C., preferbly from 0° to 40° C.

The potassium hydroxide used in the reaction is used in an amount of 1 to 20 times by mole, preferably from 5 to 7 times by mole, that of the halogenated sulfone and/or vinyl sulfone.

The reaction of (ii) according to the invention is then described.

The reaction should be effected, preferably in an atmosphere of an inert gas, in a hydrocarbon or ether solvent. Examples of the hydorcarbon solvent include toluene, benzene, hexane, cyclohexane and the like. Examples of the ether solvent include tetrahydrofuran (THF), ethyl ether, isopropyl ether, butyl ether, t-butyl methyl ether, ethylene glycol dimethyl ether, diethylene glycol dimethyl ether, triethylene glycol dimethyl ether, tetraethylene glycol dimethyl ether and the like. Of these, tetrahydrofuran is most preferred. The solvent is generally used in such a way that the concentration of the starting halogenated sulfone is in the range of about 0.05 to 2 moles/liter, but such a range is not critical.

In the general formula (5), $R^7$, $R^8$ and $R^9$ independently represent a hydrogen atom, an alkyl group which may be substituted with an oxygen atom, an aryl group or an aralkyl group. The alkyl group includes, for example, a methyl group, an ethyl group, a propyl group, a butyl group, a pentyl group, a hexyl group or the like and is preferred to have from 1 to 6 carbon atoms. The alkyl group which is substituted with an oxygen atom includes, for example, a methoxymethyl group, a 2-methoxyethoxymethyl group, a 2-(2-methoxyethoxy)ethoxymethyl group and the like. Examples of the aryl group include a phenyl group, a tolyl group, a xylyl group and the like. Examples of the aralkyl group include a benzyl group, a 1-phenylethyl group, a 2-phenylethyl group, a 3-phenylpropyl group and the like.

Examples of the alcohols of the general formula (5) include methanol, ethanol, i-propanol, t-butanol, benzyl alcohol, ethylene glycol monomethyl ethers, diethylene glycol monomethyl ethers, triethylene glycol monomethyl ethers and the like. Of these, ethylene glycol monomethyl ethers of the following formula are preferred

wherein n is an integer of 1, 2 or 3. The amount of these alcohols is preferably from 0.01 to 30 times by mole, more preferably from 0.5 to 2 times by mole, that of the halogenated sulfone of the general formula (4).

The amount of the potassium hydroxide used in the reaction is in the range of from 1 to 20 times by mole, preferably from 3 to 7 times by mole, that of the halogenated sulfone of the general formula (1).

This reaction may be carried out a temperature ranging from 0° to 120° C., preferably from 0° to 40° C.

After completion of the above reactions (i) and (ii), the reaction mixture is subjected to filtration to remove a precipitate therefrom, if necessary, to which water or an aqueous saline solution is added so as to separate an organic phase. The thus separated organic phase is subjected to a purification procedure such as recrystallization, column chromatography or the like to obtain vitamin A.

The thus obtained vitamin A is acylated according to ordinary procedures to obtain a carboxylic acid ester of vitamin A. The acylation reaction is effected by reacting the organic phase containing the vitamin A separated from the reaction mixture which is obtained by the formation reaction of vitamin A or the vitamin A separated and purified from the organic phase, with an acylating agent preferably in an organic solvent in the presence of a tertiary amine or an alkaline metal carbonate. The acylating agent includes, for example, acetic anhydride, acetyl chloride, palmitoyl chloride or the like. The amount of the acylating agent is preferably about 1 to 10 equivalents to the vitamin A. Examples of the organic solvent include hydrocarbons such as benzene, toluene and the like, halogenated hydrocarbons such as methylene chloride, 1,2-dichloroethane and the like, ethers such as diethyl ether, diisopropyl ether and the like, and esters such as ethyl acetate, butyl acetate and the like. These organic solvents are preferably used in such a way that the concentration of vitamin A is in the range of from about 0.1 to 5 moles/liter. The tertiary amine used is, for example, triethylamine, pyridine or the like and is preferably used in an amount of about 1 to 10 equivalents to the vitamin A. If the tertiary amine is used in excess, it also serves as a solvent. The alkali metal carbonate used is, for example, sodium carbonate, potassium carbonate, lithium carbonate or the like and is preferably used in an amount of from 0.1 to 5 equivalents to the acylating agent.

The reaction is favorably carried out at a temperature ranging from about $-10°$ C. to $50°$ C. After completion of the reaction, the resultant precipitate is removed by filtration from the reaction mixture, if necessary, after which dilute sulfuric acid, water, a saturated sodium hydrogencarbonate aqueous solution or a sodium hydroxide aqueous solution is added so as to separate an organic phase. The thus separated organic phase is subjected to purification procedures such as recrystallization, column chromatography and the like, thereby obtaining a carboxylic acid ester of vitamin A.

The carboxylic acid esters of vitamin A obtained according to the process of the invention include, for example, vitamin A acetate, vitamin A palmitate and the like.

The halogenated sulfone of the general formula (4) used as the starting material in the rection of (ii) according to the invention is obtained by a procedure which comprises reacting a compound of the following formula

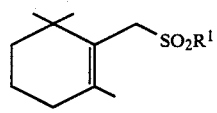

wherein $R^1$ has the same meaning as defined before, with a compound of the following formula

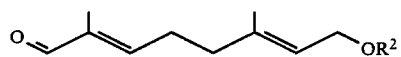

wherein $R^2$ has the same meaning as defined before, in the presence of an anionizing agent such as a Grignard reagent or an alkyl lithium to obtain a hydroxysulfone of the following formula

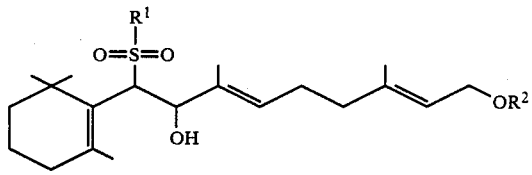

wherein $R^1$ and $R^2$ have, respectively, the same meanings as defined above, and further reacting the hydroxysulfone with a halogenating agent such as thionyl chloride, The halogenated sulfone of the general formula (1) and the vinyl sulfone of the general formula (2) used as the starting materials in the reaction of (i) of the invention are selectively obtained by treatment of the halogenated sulfone of the general formula (4) obtained by the above procedure with a metal hydroxide such as sodium hydroxide, potassium hydroxide or the like. In addition, these compounds may be prepared as a mixture.

The present invention is more particularly described by way of examples, which should not be construed as limiting the invention.

EXAMPLE 1

A 200 ml flask purged with nitrogen was charged with 9.29 g (20 mmols) of 6-chloro-1-hydroxy-3,7-dimethyl-9-(2,6,6-trimethyl-1-cyclohexen-1-yl)-9-phenylsulfonyl-2,7-nonadiene and 40 ml of toluene, followed by agitation for a while, further addition of 5.89 g (100 mmols) of powdery potassium hydroxide (purity of 95%) and 66.3 mg (0.4 mmols) of tetraethylammonium chloride and further agitation at 10° C. for 12 hours. 50 ml of a 5% saline solution was added to the reaction solution for phase separation of the solution. To the resultant organic phase was added 10 ml (105.4 mmols) of acetic anhydride and 0.9 g of sodium carbonate, followed by agitation at 40° C. for 3 hours. After addition of 100 ml of a 10% sodium hydroxide aqueous solution to the reaction solution, the resulting organic phase was separated and washed twice with 100 ml of a 5% saline solution, followed by removal of the solvent by distillation to obtain 12.8 g of a red cily substance. This oily substance was subjected to quantitative determination by high performance liquid chromatography with the result that the yield of vitamin A acetate was 80.9% and the content of the all-trans isomer in the vitamin A acetate was 94.5%. The liquid chromatographic analysis conditions were as follows.

Column: Chemcosorb 5 Si, 4.6×250 mm
Developing solvent: i-Pr$_2$O/hexane=5/95
Detector: RI

EXAMPLE 2

A 200 ml flask purged with nitrogen was charged with 8.56 g (20 mmols) of 1-hydroxy-3,7-dimethyl-9-(2,6,6-trimethyl-1-cyclohexen-1-yl)-9-phenylsulfonyl-2,6,8-nonatriene and 40 ml of toluene and agitated for a while, followed by addition of 5.89 g (100 mmols) of powdery potassium hydroxide (purity of 95%) and 66.3 mg (0.4 mmols) of tetraethylammonium chloride and agitation at 10° C. for further 12 hours. 50 ml of a 5% saline solution was added to the reaction solution for phase separation. The resultant organic phase was charged with 10 ml (105.4 mmols) of acetic anhydride and 0.9 g of sodium carbonate and agitated at 40° C. for 3 hours. After addition of 100 ml of a 10% sodium hydroxide aqueous soltuion to the reaction solution, the organic phase was separated and washed twice with 100 ml of a 5% saline solution, followed by removal of the solvent by distillation to obtain 12.6 g of a red oily substance. This oily substance was quantitatively determined by the use of high performance liquid chromatography, revealing that the yield of vitamin A acetate was 78.9%. In addition, it was found that the content of the all-trans isomer in the vitamin A acetate was 94.3%.

EXAMPLE 3

A 200 ml flask purged with nitrogen was charged with a mixture of 2.6 g (5.6 mmols) of 6-chloro-1-hydroxy-3,7-dimethyl-9-(2,6,6-trimethyl-1-cyclohexen-1-yl)-9-phenylsulfonyl-2,7-nonadiene and 6.16 g (14.4 mmols) of 1-hydroxy-3,7-dimethyl-9-(2,6,6-trimethyl-1-cyclohexen-1-yl)-9-phenylsuflonyl-2,6,8-nonatriene and 40 ml of toluene and agitated for a while, followed by addition of 5.89 g (100 mmols) of powdery potassium hydroxide (purity of 95%) and 66.3 mg (0.4 mmols) of tetraethylammonium chloride and agitation at 10° C. for further 12 hours. 50 ml of a 5% saline solution was added to the reaction solution for phase separation. The resultant organic phase was charged with 10 ml (105.4 mmols) of acetic anhydride and 0.9 g of sodium carbonate and agitated at 40° C. for 3 hours. After addition of 100 ml of a 10% sodium hydroxide aqueous solution to the reaction solution, the organic phase was separated and washed twice with 100 ml of a 5% saline solution, followed by removal of the solvent by distillation to obtain 12.3 g of a red oily substance. This oily substance was quantitatively determined by the use of high performance liquid chromatography, revealing that the yield of vitamin A acetate was 77.9%. In addition, it was found that the content of the all-trans isomer in the vitamin A acetate was 94.5%.

EXAMPLE 4

A 200 ml flask purged with nitrogen was charged with a mixture of 2.6 g (5.6 mmols) of 6-chloro-1-hydroxy-3,7-dimethyl-9-(2,6,6-trimethyl-1-cyclohexen-1-yl)-9-phenylsulfonyl-2,7-nonadiene and 6.16 g (14.4 mmols) of 1-hydroxy-3,7-dimethyl-9-(2,6,6-trimethyl-1-cyclohexen-1-yl)-9-phenylsulfonyl-2,6,8-nonatriene and 40 ml of toluene and agitated for a while, followed by addition of 5.89 g (100 mmols) of powdery potassium hydroxide (purity of 95%) and 71 mg (0.4 mmols) of 12-crown-4 and agitation at 10° C. for further 12 hours. 50 ml of a 5% saline solution was added to the reaction solution for phase separation. The resultant organic phase was charged with 10 ml (105.4 mmols) of acetic anhydride and 0.9 g of sodium carbonate and agitated at 40° C. for 3 hours. After addition of 100 ml of a 10% sodium hydroxide aqueous solution to the reaction solution, the organic phase was separated and washed twice with 100 ml of a 5% saline solution, followed by removal of the solvent by distillation to obtain 13.1 g of a red oily substance. This oily substance was quantitatively determined by the use of high performance liquid chromatography, revealing that the yield of vitamin A acetate was 78.2%. In addition, it was found that the content of all-trans isomer in the vitamin A acetate was 93.8%.

EXAMPLE 5

A 300 ml flask purged with nitrogen was charged with 22.32 g (44 mmols) of 1-acetoxy-6-chloro-3,7-dimethyl-9-(2,6,6-trimethyl-1-cyclohexen-1-yl)-9-phenylsulfonyl-2,7-nonadiene and 75 ml of THF and agitated for a while, to which 370 mg (1.76 mmols) of tetraethylammonium chloride, 3.34 g (44 mmols) of 2-methoxyethanol and 13 g (220 mmols) of powdery potassium hydroxide (purity of 95%) were added and agitated at 30° C. for 6.5 hours. To the reaction solution were further added 100 ml of toluene and 50 ml of a 5% saline solution for phase separation. The resultant organic phase was charged with 20.2 ml (213 mmols) of acetic anhydride and 1.87 g of sodium carbonate and agitated at 40° C. for 3 hours. After addition of 200 ml of a 10% sodium hydroxide aqueous solution to the reaction solution, the organic phase was separated and washed twice with 100 ml of a 5% saline solution, followed by removal of the solvent by distillation to obtain 22 g of a red oily substance.

This oily substance was quantitatively determined by the use of high performance liquid chromatography, revealing that the yield of vitamin A acetate was 82.4% based on the 1-acetoxy-6-chloro-3,7-dimethyl-9-(2,6,6-trimethyl-1-cyclohexen-1-yl)-9-phenylsulfonyl-2,7-nonadiene. In addition, it was found that the content of all-trans isomer in the vitamin A acetate was 94.6%.

EXAMPLE 6

A 300 ml flask purged with nitrogen was charged with 22.32 g (44 mmols) of 1-acetoxy-6-chloro-3,7-dimethyl-9-(2,6,6-trimethyl-1-cyclohexen-1-yl)-9-phenylsulfonyl-2,7-nonadiene and 100 ml of toluene and agitated for a while, to which 567 mg (1.76 mmols) of tetra-n-butylammonium chloride, 1.41 g (44 mmols) of methanol and 13 g (220 mmols) of powdery potassium hydroxide (purity of 95%) were added and agitated at 40° C. for 11 hours. To the reaction solution were further added 50 ml of a 5% saline solution for phase separation. The resultant organic phase was charged with 20.2 ml (213 mmols) of acetic anhydride and 1.87 g of sodium carbonate and agitated at 40° C. for 3 hours. After addition of 200 ml of a 10% sodium hydroxide aqueous solution to the reaction solution, the organic phase was separated and washed twice with 100 ml of a 5% saline solution, followed by removal of the solvent by distillation to obtain 23.01 g of a red oily substance. This oily substance was quantitatively determined by the use of high performance liquid chromatography, revealing that the yield of vitamin A acetate was 79.8% based on the 1-acetoxy-6-chloro-3,7-dimethyl-9-(2,6,6-trimethyl-1-cyclohexen-1-yl)-9-phenylsulfonyl-2,7-nonadiene. In addition, it was found that the content of all-trans isomer in the vitamin A acetate was 92.0%.

COMPARATIVE EXAMPLE

A 50 ml flask purged with argon was charged with 0.49 g (0.97 mmols) of 1-acetoxy-6-chloro-3,7-dimethyl-9-(2,6,6-trimethyl-1-cyclohexen-1-yl)-9-phenylsulfonyl-2,7-nonadiene and 15 ml of cyclohexane. The mixture was stirred for a while, and 0.66 g (10 mmols) of powdery potassium hydroxide (purity of 85%) was added. The mixture was stirred at 65° C. for 1.5 hours, and further at the refluxing temperature for 2 hours. After cooling, 30 ml of diisopropyl ether and 15 ml of a saturated aqueous solution of ammonium chloride were added to the reaction mixture. The organic phase was separated, and the aqueous phase was extracted with 20 ml of diisopropyl ether. The extract was washed with a saturated aqueous solution of ammonium chloride, and dried over anhydrous magnesium sulfate. The organic solvent was evaporated from the organic phase, and the residue, together with 5 ml of a 0.05% by weight hexane solution of 2,6-di-t-butyl-4-methylphenol and 1.1 ml of triethylamine, was put in a 100 ml flask purged with argon. Under ice bath cooling, 0.68 ml of acetic anhydride was added to the mixture. The mixture was stirred at room temperature for 1 day. To the reaction mixture were added 50 ml of hexane and 10 ml of a saturated aqueous solution of sodium bicarbonate. The mixture was stirred for a while, and the hexane phase was separated. The hexane phase was washed with a saturated aqueous solution of sodium bicarbonate, and dried over anhydrous magnesium sulfate. Hexane was evaporated from the hexane solution to give 0.36 g of a red oily product. The resulting vitamin A acetate was quantified by high performance liquid chromatography. It was found that the yield of vitamin A was 64% based on the 1-acetoxy-6-chloro-3,7-dimethyl-9-(2,6,6-trimethyl-1-cyclohexen-1-yl)-9-phenylsulfonyl-2,7-nonadiene, and its all trans content was 90%.

What is claimed is:

1. A process for producing vitamin A or its carboxylic acid ester, which comprises (i) treating a halogenated sulfone of the general formula (1)

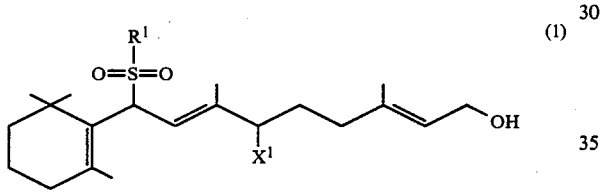

wherein $R^1$ represents a phenyl group which may be substituted by lower alkyl, halogen or lower alkoxy, and $X^1$ represents a halogen atom, and/or a vinyl sulfone of the general formula (2)

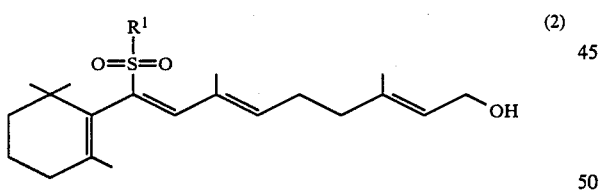

wherein $R^1$ has the same meaning as defined above, with potassium hydroxide in a hydrocarbon solvent in the presence of a quaternary ammonium salt of the general formula (3) or a crown ether

wherein $R^3$, $R^4$, $R^5$ and $R^6$ are the same or different and represents an alkyl group of 1–20 carbon atoms or an aralkyl group of 7–9 carbon atoms, and X represents a halogen atom, a lower alkoxy group, a lower alkylcarbonyloxy or a benzoyloxy group, a hydrogensulfate or a hydroxyl group, and, if necessary, acylating the resultant vitamin A.

2. A process according to claim 1, wherein the potassium hydroxide is used in an amount of 1 to 20 times by mole that of the halogenated sulfone and/or vinyl sulfone.

3. A process according to claim 1, wherein the treatment is effected at a temperature of from −10° C. to 100° C.

4. A process according to claim 1, wherein the treatment is effected in an atmosphere of an inert gas.

5. A process for producing vitamin A or its carboxylic acid ester, which comprises treating a halogenated sulfone of the general formula (4)

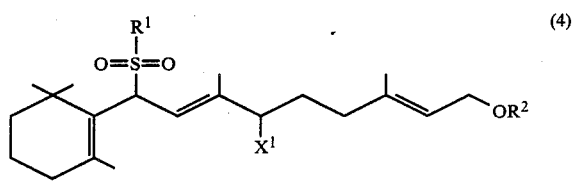

wherein $R^1$ represents a phenyl group which may be substituted by lower alkyl, halogen or lower alkoxy, $R^2$ represents a lower acyl group and $X^1$ represents a halogen atom, with potassium hydroxide in a hydrocarbon or ether solvent in the presence of a quaternary ammonium salt of the formula (3)

wherein $R^3$, $R^4$, $R^5$ and $R^6$ are the same or different and represents an alkyl group of 1–20 carbon atoms or an aralkyl group of 7–9 carbon atoms, and X represents a halogen atom, a lower alkoxy group, a lower alkylcarbonyloxy or a benzoyloxy group, a hydrogensulfate or a hydroxyl group, and an alcohol of the general formula (5)

wherein $R^7$, $R^8$ and $R^9$ are the same or different and represent a hydrogen atom, an alkyl group of 1–6 carbon atoms which may be substituted with an oxygen atom, an aryl group of 6–8 carbon atoms or an aralkyl group of 7–9 carbon atoms, and, if necessary, acylating the resultant vitamin A.

6. A process according to claim 5 wherein the potassium hydroxide is used in an amount of from 1 to 20 times by mole that of the halogenated sulfone.

7. A process according to claim 5, wherein the treatment is effected at a temperature of from 0° C. to 120° C.

8. A process according to claim 5, wherein the treatment is effected in an atmosphere of an inert gas.

9. A process according to claim 5, wherein the alcohol of the general formula (5) is an ethylene glycol monomethyl ether of the following formula

wherein n is an integer of 1, 2 or 3.

10. A process according to claim 5, wherein the ether solvent is tetrahydrofuran.

11. A process according to claim 1, wherein the hydrocarbon solvent is toluene, benzene, hexane or cyclohexane.

12. A process according to claim 5, wherein the hydrocarbon solvent is toluene, benzene, hexane or cyclohexane, and the ether solvent is tetrahydrofuran, ethyl ether, isopropyl ether, butyl ether, t-butylmethyl ether, ethylene glycol dimethyl ether, diethylene glycol dimethyl ether, triethylene glycol dimethyl ether or tetraethylene glycol dimethyl ether.

* * * * *